United States Patent
Chen

(10) Patent No.: US 12,033,744 B2
(45) Date of Patent: Jul. 9, 2024

(54) DATA-DRIVEN RANKING AND RECOMMENDATION SYSTEM USING NEURAL NETWORK-BASED LEARNING MODELS FOR MEDICAL FACILITIES AND PROVIDERS

(71) Applicant: LINKSciences LLC, Baltimore, MD (US)

(72) Inventor: Fenghao Chen, Lutherville, MD (US)

(73) Assignee: LINKSCIENCES LLC, Baltimore, MD (US)

( * ) Notice: Subject to any disclaimer, the term of this patent is extended or adjusted under 35 U.S.C. 154(b) by 592 days.

(21) Appl. No.: 17/105,104

(22) Filed: Nov. 25, 2020

(65) Prior Publication Data

US 2021/0158949 A1    May 27, 2021

Related U.S. Application Data

(60) Provisional application No. 62/939,818, filed on Nov. 25, 2019.

(51) Int. Cl.
*G16H 40/20* (2018.01)
*G06N 3/04* (2023.01)
(Continued)

(52) U.S. Cl.
CPC .............. *G16H 40/20* (2018.01); *G06N 3/04* (2013.01); *G06N 3/08* (2013.01);
(Continued)

(58) Field of Classification Search
CPC ........ G16H 40/20; G16H 50/20; G16H 70/20; G16H 70/60; G06N 3/04; G06N 3/08; G06N 3/044; G06Q 10/06393
See application file for complete search history.

(56) References Cited

U.S. PATENT DOCUMENTS

| | | | |
|---|---|---|---|
| 8,560,346 B2 * | 10/2013 | Bundschus | G16H 40/20 705/2 |
| 2007/0088577 A1 * | 4/2007 | Carter | G16H 10/60 705/3 |

(Continued)

OTHER PUBLICATIONS

A. Taylor, Larry Ray. "A Model for the Classification of Digital Trust in Online Healthcare Social Networks." Order No. 10277065 Fielding Graduate University, 2017. Ann Arbor. (Year: 2017).*

*Primary Examiner* — Amber A Misiaszek
(74) *Attorney, Agent, or Firm* — Getech Law LLC; Jun Ye

(57) ABSTRACT

Systems, methods and computer program products are provided for evaluating a healthcare center. The evaluation of the healthcare center may be performed based on an expertise score associated with the healthcare center. The expertise score may be obtained by obtaining raw data from a plurality of data sources providing healthcare data, cleaning and organizing the raw data on the basis of one or more expertise domains in the healthcare sector to obtain organized data values for each expertise domain, obtaining a weight matrix specifying a weight for each organized data value in the one or more expertise domains, and calculating the expertise score on the basis of the organized data values and the weight matrix. The weight matrix may be obtained using a machine learning model. Further, the expertise score may be calculated at a disease level or at a specialty level for the designated healthcare center.

20 Claims, 8 Drawing Sheets

(51) Int. Cl.
*G06N 3/08* (2023.01)
*G06Q 10/0639* (2023.01)
*G16H 50/20* (2018.01)
*G16H 70/20* (2018.01)
*G16H 70/60* (2018.01)

(52) U.S. Cl.
CPC ....... *G06Q 10/06393* (2013.01); *G16H 50/20* (2018.01); *G16H 70/20* (2018.01); *G16H 70/60* (2018.01)

(56) References Cited

U.S. PATENT DOCUMENTS

| | | | |
|---|---|---|---|
| 2012/0016690 A1* | 1/2012 | Ramarajan | G16Z 99/00 705/2 |
| 2016/0034648 A1* | 2/2016 | Mohlenbrock | G16H 40/20 705/3 |
| 2016/0203217 A1* | 7/2016 | Anisingaraju | G06Q 10/067 707/738 |
| 2018/0144825 A1* | 5/2018 | Xu | G16H 40/20 |
| 2019/0102721 A1* | 4/2019 | Foster | G16H 40/20 |

* cited by examiner

Table 1

| Symbol | Description |
|---|---|
| X | A specific disease, disorder, or health condition |
| Y | A branch of medicine or surgery with similar characteristics biologically, or clinically. |
| H | Hospital, medical center or provider institution |
| ED | Data matrix for Expertise Domain:<br>• ED1 represents the data from scientific research domain for disease X<br>• ED2 represents the data from translational medicine domain for disease X<br>• ED3 represents the data from clinical practice domain for disease X |
| W | Expertise coefficients in weighing matrix for designated health condition, disease or disorder (X). The coefficients are similar or constant for diseases associated with the designated disease area. The value is to be determined using machine learning models. |

FIG. 5

DATA-DRIVEN RANKING AND RECOMMENDATION SYSTEM USING NEURAL NETWORK-BASED LEARNING MODELS FOR MEDICAL FACILITIES AND PROVIDERS

PRIORITY APPLICATION

This application claims the benefit of and priority to U.S. Provisional Patent Application No. 62/939,818, filed Nov. 25, 2019, the entire contents of which are incorporated herein by reference.

TECHNOLOGICAL FIELD

The present disclosure generally relates to expertise scoring of healthcare centers, and more specifically relates to, use of a neural network for expertise scoring of healthcare centers.

BACKGROUND

Healthcare centers are healthcare institutions, such as hospitals, clinics, nursing homes and the like, that provide patient treatment with specialized medical and nursing staff and medical equipment. Hospitals may also include academic health centers (AHCs), which have played leadership roles in medical innovation, scientific research, and clinical practice. AHCs have also been playing a pivotal role in healthcare center evaluations, on account of being looked upon as advisers for end users for critical health related decision making processes. Such critical decision making includes choosing the best fit healthcare center for their treatment, in case of a diagnosis related to an illness. The decision becomes more critical if the illness is life threatening, and thus, accurate, reliable and up-to-date information about evaluation of various healthcare centers is of utmost importance.

Currently, many such decisions are based on human based factors, such as doctor's preference, family consultations, and hospital reputation. In the past, several hospital rankings and ratings have been developed to augment the bases for such important decisions. These rankings and ratings are derived based on a variety of aspects, such as reputation, performance, safety, and service quality. However, it has been found through various studies that these rankings and ratings suffer from high inconsistencies in data, and also lack transparency and specifically tailored to or focused on expertise of the healthcare centers and thus, lack of granularity regarding specific disease areas or diseases. Further, the data sources from which data for calculating such rankings and ratings are highly fragmented, oftentimes biased, and not reliable. Also, many such rankings have become obsolete because of lagging behind in catching up with the data explosion revolution because of use of outdated technical tools and models.

Thus, there is a need for broader coverage and clinically stronger and medically relevant information and data sources, technically advanced methodologies for evaluation of healthcare centers.

BRIEF SUMMARY

Evaluation of healthcare centers, such as hospitals, is a critical factor for users, such as patients, for choosing the right hospital for right treatment. The current approaches for hospital evaluations have been criticized for a long time, because of having evident bias towards certain medial facilities and healthcare centers. Further, the scoring and rating of healthcare centers by the previously known methods is not reliable as they are mostly based on public medical data that was difficult to access, and a lack of quality data limited the usefulness of any such ratings. As a result, such evaluations have relied on reputation of healthcare centers, resulting in that a small group of prominent hospitals in each specialty receives such high scores that they automatically rise to the top of the rankings, regardless of the structure or outcome score. Accordingly, in order to provide accurate and reliable information on hospital's performance, treatment and other factors, more reliable and granular scoring mechanisms are needed, that are based on good quality and reliable data. Example embodiments of the present disclosure provide a system, a method, and a computer program product for evaluating a healthcare center by determining an expertise score for the healthcare center, using reliable data from a plurality of data sources. The embodiments of the present disclosure may also determine whether a health center is top rated for the expertise of a specific disease. Further, the data is analyzed using advanced machine learning and neural network algorithms to provide accurate, reliable, and granular scoring and prediction outcomes for hospital evaluations. To that end, the scoring can even be done at disease area level or specialty area level, for the healthcare center under evaluation.

Some example embodiments disclosed herein provide a computer-implemented method for determining an expertise score for a healthcare center. The healthcare center may be a hospital, a clinic, a medical research and care institution and the like. The method comprises extracting raw data values from a plurality of data sources. The raw data may then be stored in the form of both structured and unstructured data in data lakes. The method further comprises organizing, using a processor, the extracted raw data values into one or more expertise domains (EDs) to obtain organized data value. The one or more EDs comprise at least a scientific research expertise domain (SR or ED1), a translational medicine expertise domain (TM or ED2), a clinical practice expertise domain (CP or ED3), or a combination thereof. The method further comprises normalizing the organized data values based on a set of features to obtain a first data matrix for each of the one or more EDs. The first data matrix for each of the one or more EDs comprises one or more parametric data values associated with a health condition. The health condition could be a disease area for which treatment service is provided by the healthcare center. The health condition could also be a specialty area of the healthcare center. The method further comprises obtaining, using a machine learning model executed by the processor, a weight matrix corresponding to each first data matrix for each of the one or more EDs. The weight matrix comprises a set of coefficients determining an extent of contribution of each of the one or more parametric data values associated with the health condition for expertise score determination. The weight matrix may be precomputed using the machine learning model. The machine learning model may be trained based on the raw data, after proper cleansing, preparation, labelling and pairing. The method further comprises calculating, using the processor, the expertise score for the healthcare center based on the obtained first data matrix for each of the one or more EDs and the weight matrix corresponding to each first data matrix for each of the one or more EDs. The expertise score may be used by a user, such as a patient for evaluating the healthcare center, at the time of critical decision making process (such as during an illness needing treatment).

According to another embodiment, a system for determining an expertise score for a healthcare center is provided. The system comprising a memory configured to store computer-executable instructions and one or more processors configured to execute the computer-executable instructions to extract raw data values from a plurality of data sources. The one or more processors are further configured to organize the extracted raw data values into one or more expertise domains (EDs) to obtain organized data values, wherein the one or more EDs comprise at least a scientific research expertise domain (SR or ED1), a translational medicine expertise domain (TM or ED2), a clinical practice expertise domain (CP or ED3), or a combination thereof. The one or more processors are further configured to normalize the organized data values based on a set of features to obtain a first data matrix for each of the one or more EDs, wherein the corresponding first data matrix for each of the one or more EDs comprises one or more parametric data values associated with a health condition. The one or more processors are further configured to obtain, using a machine learning model, a weight matrix corresponding to each first data matrix for each of the one or more EDs, wherein the weight matrix comprises a set of coefficients determining an extent of each of the one or more parametric data values associated with the health condition for expertise score determination. Further, the one or more processors are configured to calculate the expertise score for the healthcare center based on the obtained first data matrix for each of the one or more EDs and the weight matrix corresponding to each first data matrix for each of the one or more EDs.

According to yet another embodiment, a computer programmable product comprising a non-transitory computer readable medium having stored thereon computer executable instructions which when executed by one or more processors, cause the one or more processors to carry out operations for determining an expertise score for a healthcare center, the operations comprising obtaining, extracting raw data values from a plurality of data sources. The operations further comprising organizing, the extracted raw data values into one or more expertise domains (EDs) to obtain organized data values, wherein the one or more EDs comprise at least a scientific research expertise domain (SR or ED1), a translational medicine expertise domain (TM or ED2), a clinical practice expertise domain (CP or ED3), or a combination thereof. The operations further comprising normalizing the organized data values based on a set of features to obtain a first data matrix for each of the one or more EDs, wherein the corresponding first data matrix for each of the one or more EDs comprises one or more parametric data values associated with a health condition. The operations further comprising obtaining, using a machine learning model, a weight matrix corresponding to each first data matrix for each of the one or more EDs, wherein the weight matrix comprises a set of coefficients determining an extent of each of the one or more parametric data values associated with the health condition for expertise score determination. The operations further comprising calculating, the expertise score for the healthcare center based on the obtained first data matrix for each of the one or more EDs and the weight matrix corresponding to each first data matrix for each of the one or more EDs.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Figure 1:
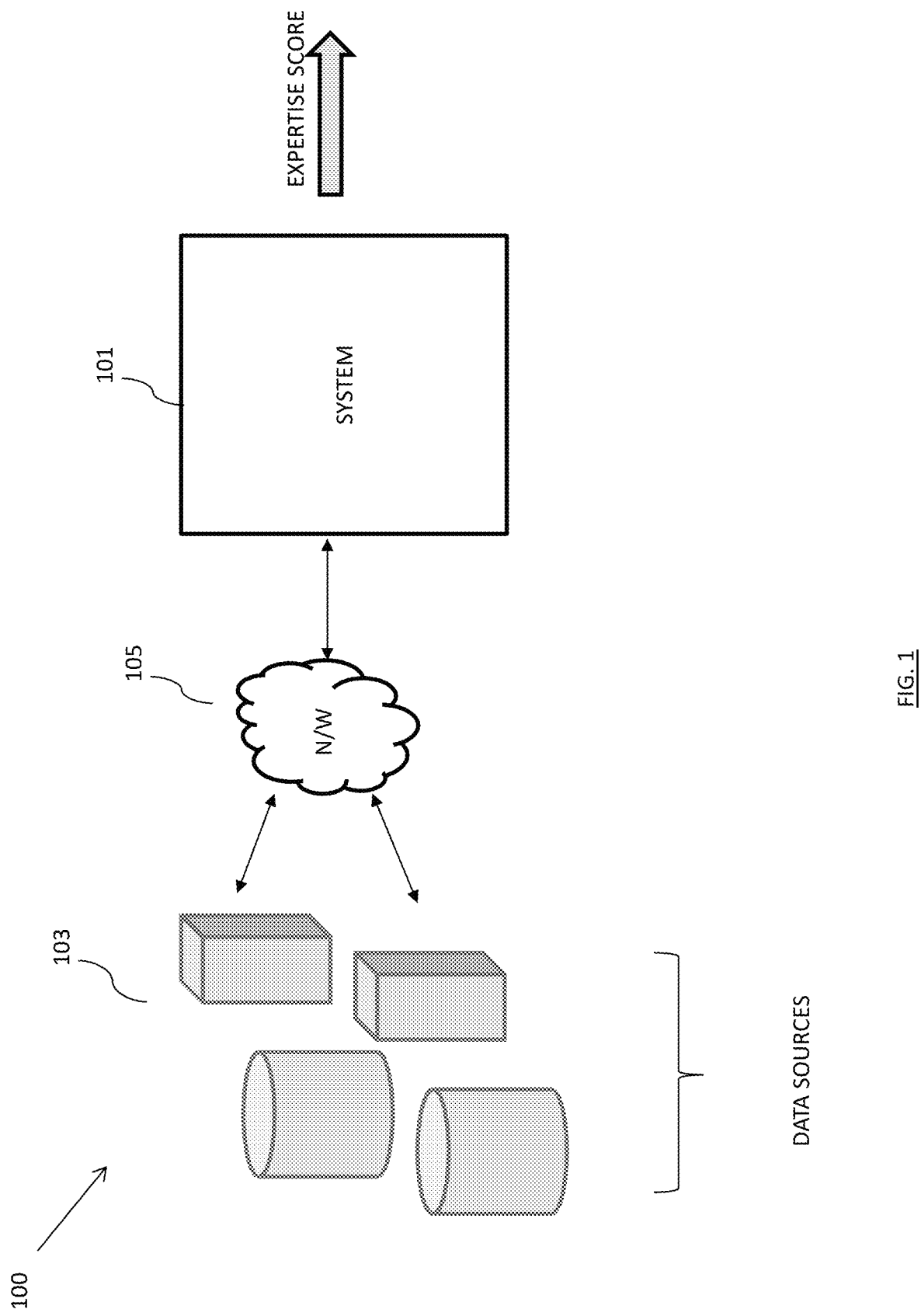
Figure 2:
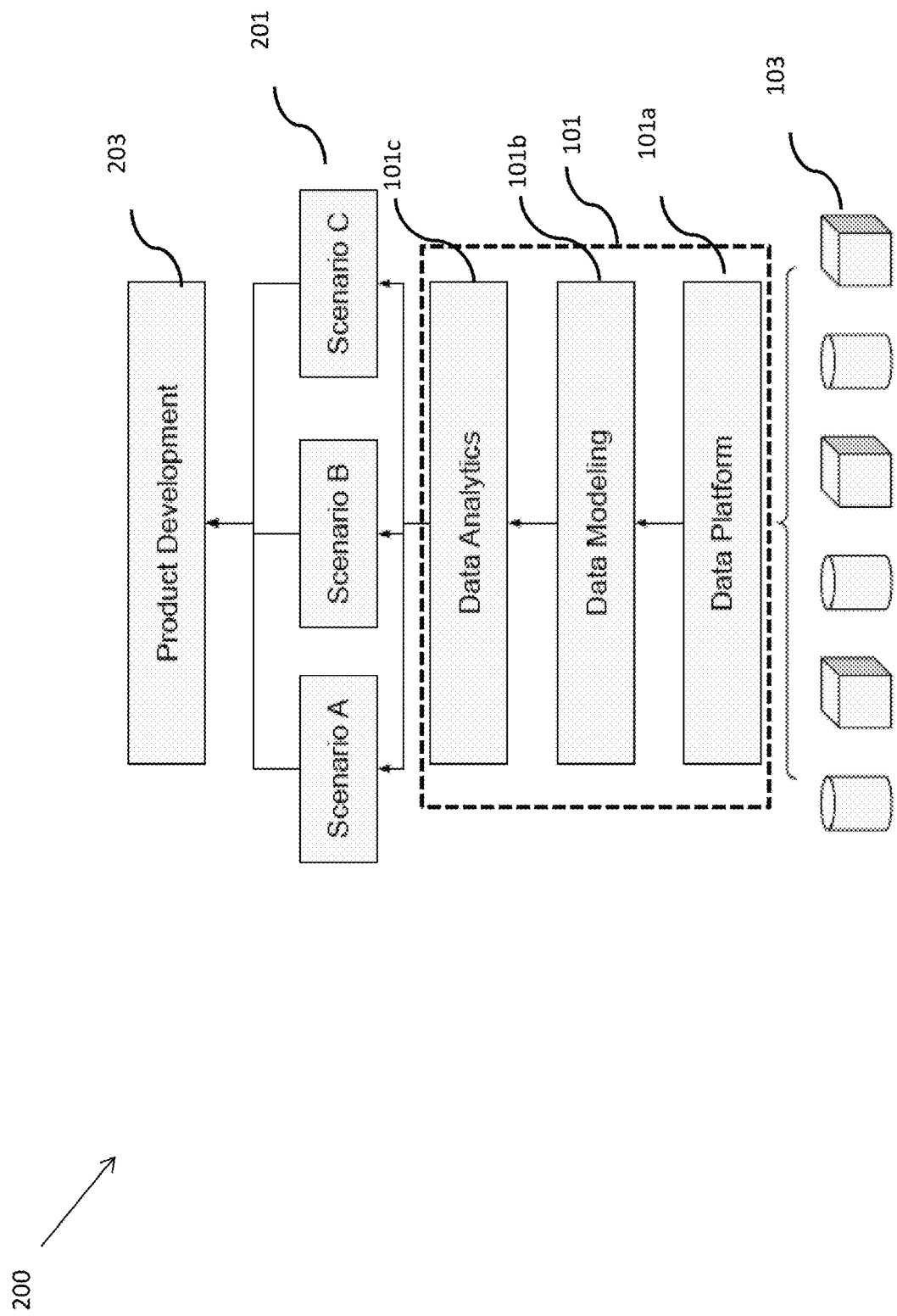
Figure 3:
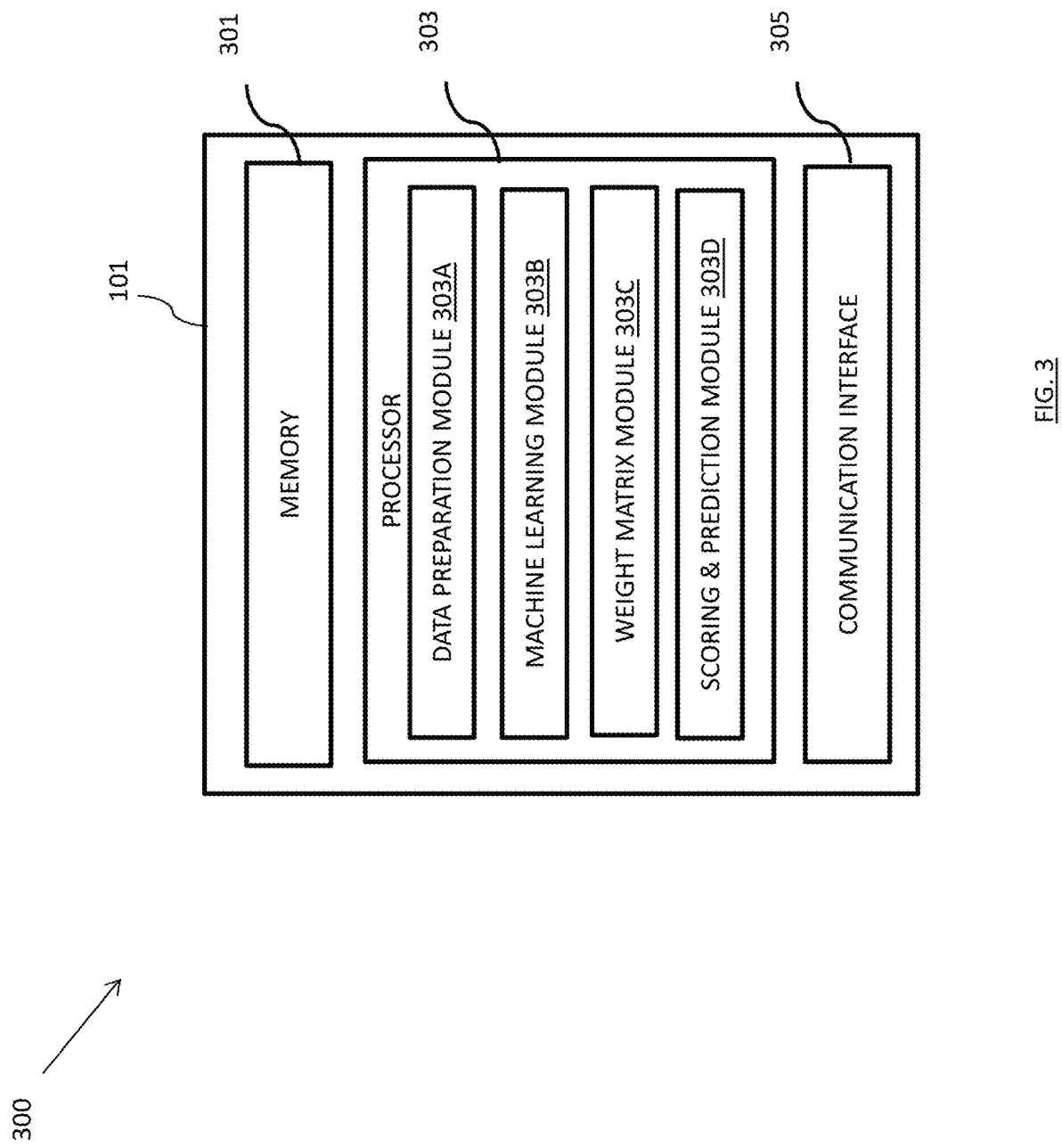
Figure 4:
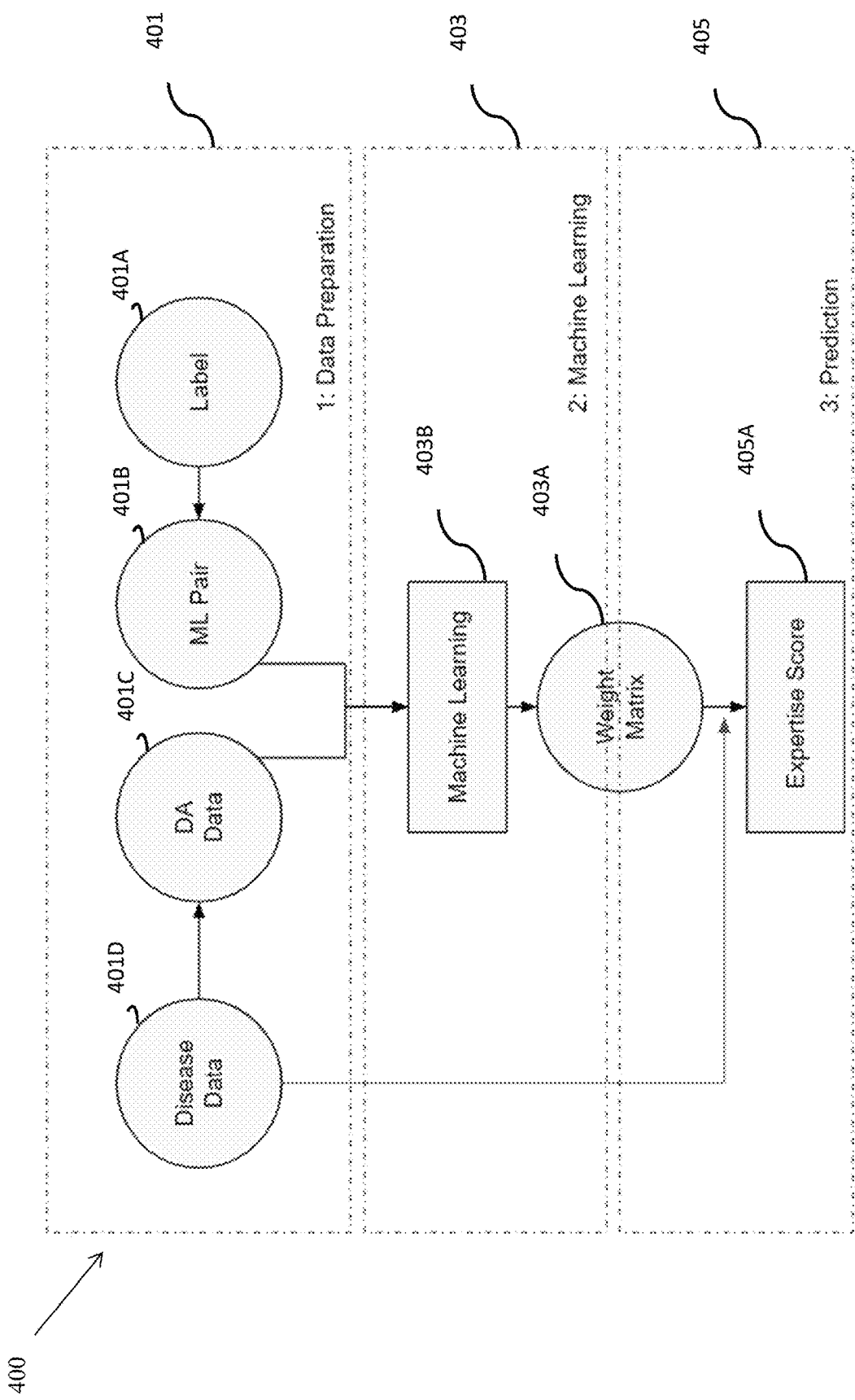
Figure 6:
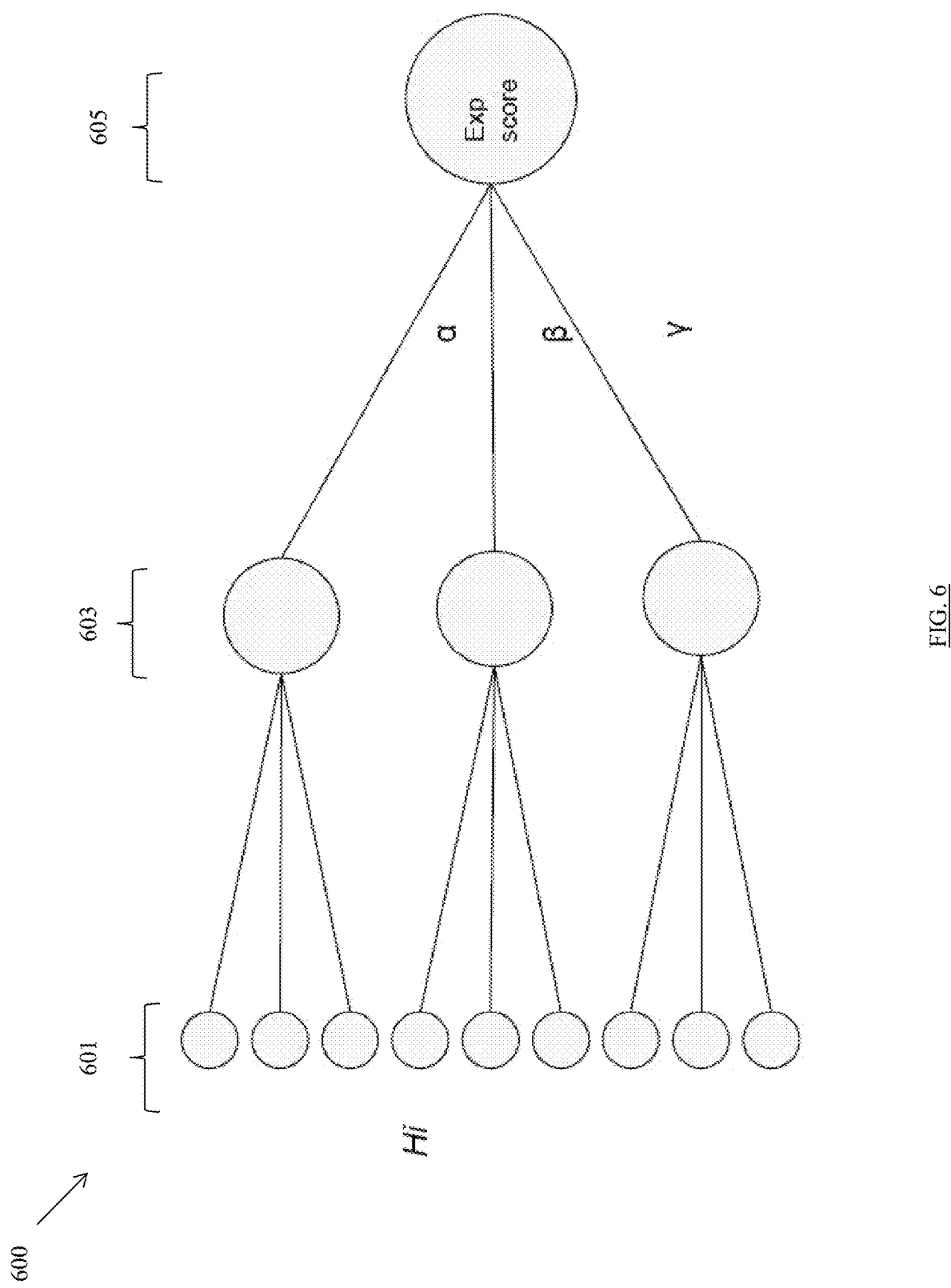
Figure 7:
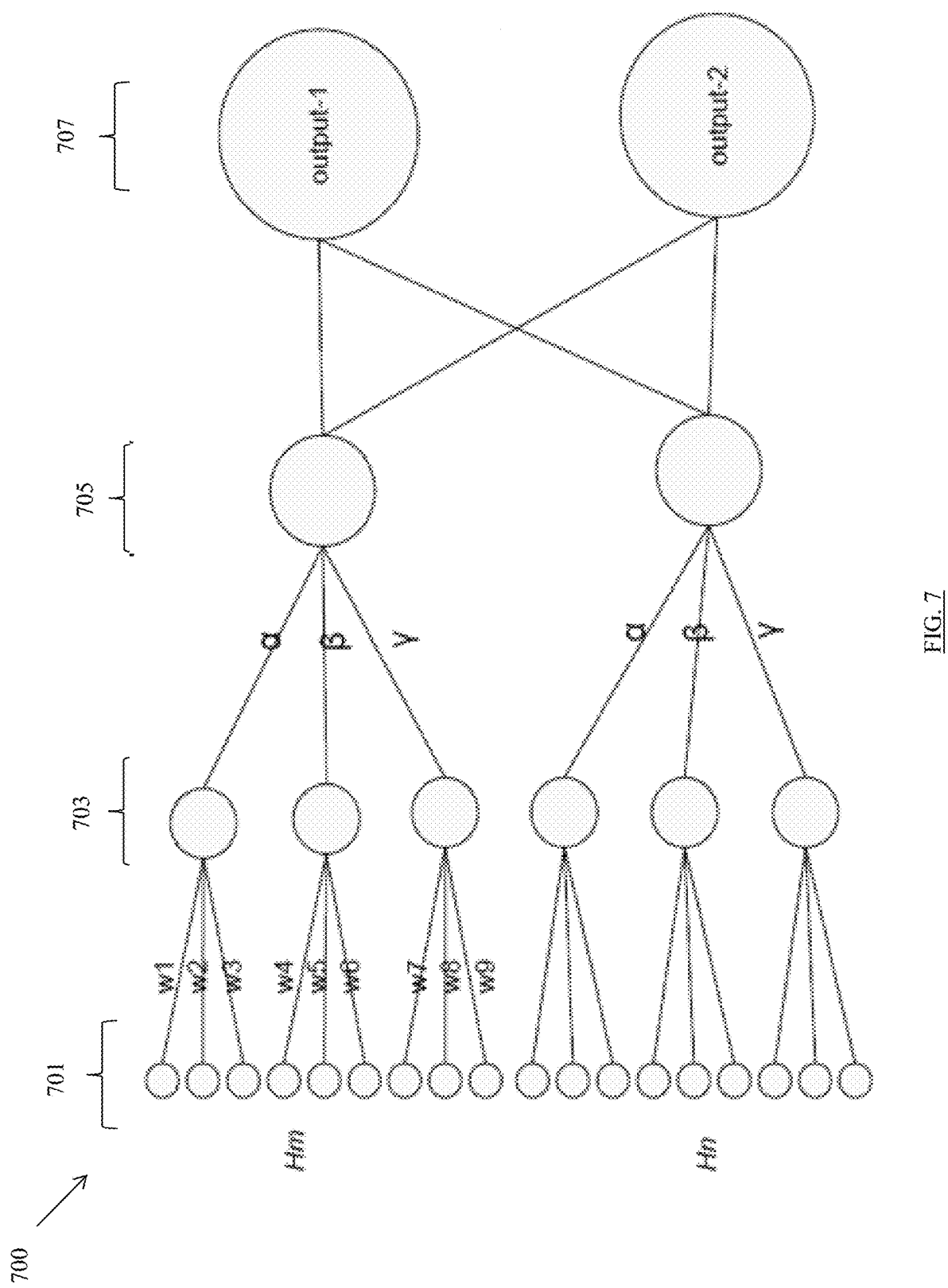
Figure 8:
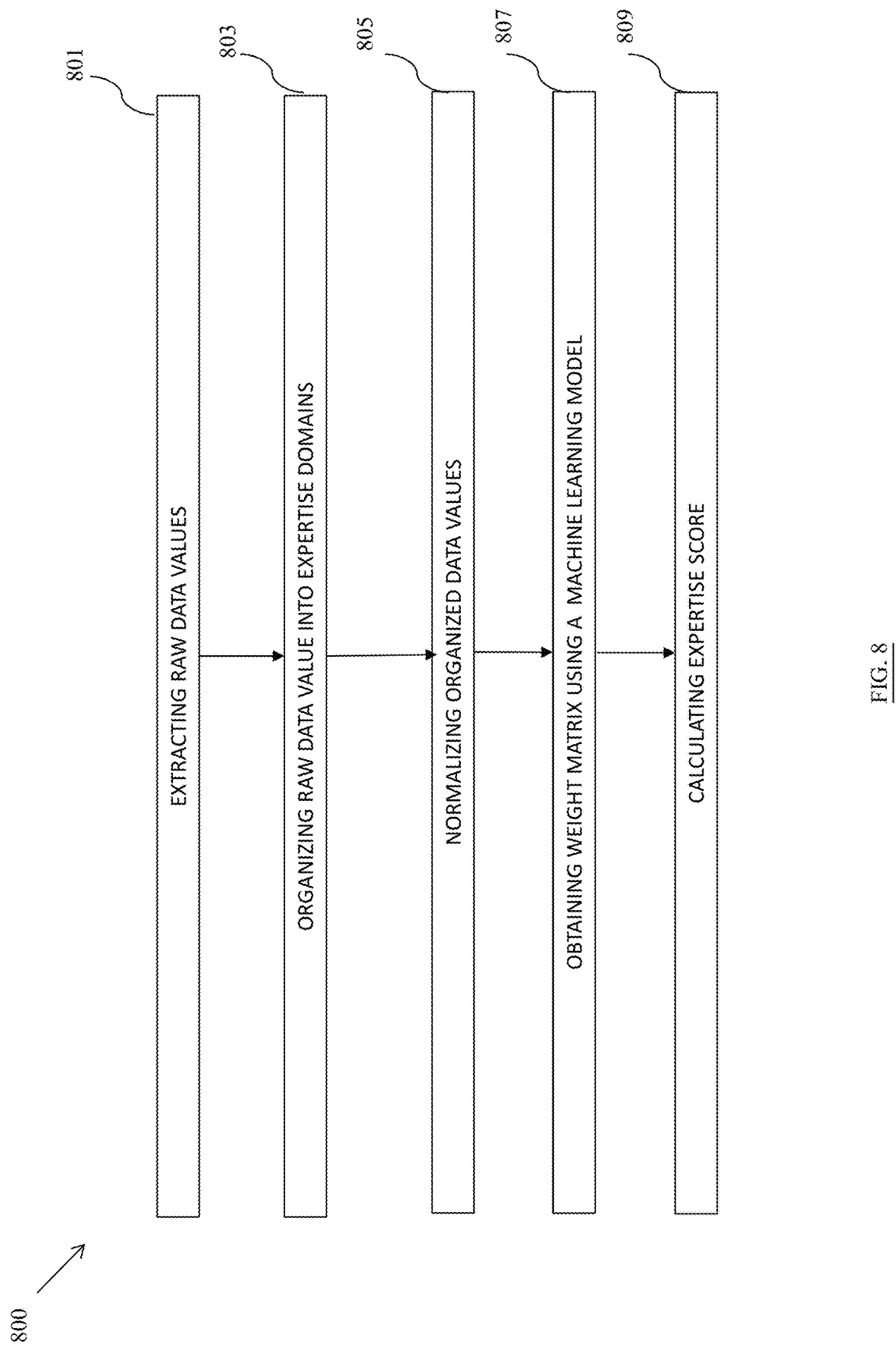

Having thus described example embodiments of the invention in general terms, reference will now be made to the accompanying drawings, which are not necessarily drawn to scale, and wherein:

FIG. 1 illustrates a schematic diagram of a network environment of a system for evaluating a healthcare center, in accordance with an example embodiment;

FIG. 2 illustrates a block diagram of an architecture of the system of FIG. 1 for evaluating a healthcare center, in accordance with an example embodiment;

FIG. 3 illustrates a block diagram of the system of FIG. 1 for evaluating a healthcare center, in accordance with an example embodiment;

FIG. 4 illustrates a block diagram of a series of operations performed by the system of FIG. 1 for calculating an expertise score for a healthcare, in accordance with one or more example embodiments;

FIG. 5 illustrates an exemplary table Table 1, showing various variables used in expertise score calculation for a healthcare center, in accordance with one or more example embodiments;

FIG. 6 illustrates an exemplary block diagram of a differential tree structure neural network model used for expertise score calculation for a healthcare center, in accordance with an example embodiment;

FIG. 7 illustrates an exemplary block diagram of a differential tree structure paired neural network model used for expertise score comparison between two healthcare centers, in accordance with an example embodiment; and FIG. 8 illustrates an exemplary flow diagram of a method for expertise score determination of a healthcare center, in accordance with an example embodiment.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. In other instances, systems, apparatuses and methods are shown in block diagram form only in order to avoid obscuring the present disclosure.

Reference in this specification to "one embodiment" or "an embodiment" means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Further, the terms "a" and "an" herein do not denote a limitation of quantity, but rather denote the presence of at least one of the referenced items. Moreover, various features are described which may be exhibited by some embodiments and not by others. Similarly, various requirements are described which may be requirements for some embodiments but not for other embodiments.

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information," and similar terms may be used interchangeably to refer to data capable of being transmitted, received and/or stored in accordance with embodiments of the present invention. Thus, use of any such terms should not be taken to limit the spirit and scope of embodiments of the present invention.

Additionally, as used herein, the term 'circuitry' may refer to (a) hardware-only circuit implementations (for example, implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a microprocessor(s) or a portion of a microprocessor(s), that require software or firmware for operation even if the software or firmware is not physically present. This definition of 'circuitry' applies to all uses of this term herein, including in any claims. As a further example, as used herein, the term 'circuitry' also includes an implementation comprising one or more processors and/or portion(s) thereof and accompanying software and/or firmware. As another example, the term 'circuitry' as used herein also includes, for example, a baseband integrated circuit or applications processor integrated circuit for a mobile phone or a similar integrated circuit in a server, a cellular network device, other network device, and/or other computing device.

As defined herein, a "computer-readable storage medium," which refers to a non-transitory physical storage medium (for example, volatile or non-volatile memory device), can be differentiated from a "computer-readable transmission medium," which refers to an electromagnetic signal.

The embodiments are described herein for illustrative purposes and are subject to many variations. It is understood that various omissions and substitutions of equivalents are contemplated as circumstances may suggest or render expedient but are intended to cover the application or implementation without departing from the spirit or the scope of the present disclosure. Further, it is to be understood that the phraseology and terminology employed herein are for the purpose of the description and should not be regarded as limiting. Any heading utilized within this description is for convenience only and has no legal or limiting effect.

Some embodiments relate to a method, a system, and a computer-programmable product describing techniques for evaluation of healthcare centers. A healthcare center as disclosed herein, may include a healthcare and treatment facility, including but not limited to a hospital, a clinic, a medical research and treatment center, a medical institution, a nursing home, an infirmary, and the like. The evaluation of the healthcare center as described herein is done by calculating an expertise score for the healthcare center. The expertise score is calculated at high granular level, such as at disease area level or at specialty area level. The expertise score may be used for evaluating the healthcare center, for comparison of two healthcare centers, for providing recommendations to the users regarding healthcare decisions, for generating institutional profiles of the healthcare centers, for providing a visualization of the capabilities of the healthcare center on a dashboard user interface, and the like among others.

As compared to the healthcare center evaluation methods and systems available in the art, the methods and systems of the present disclosure provide a more accurate, reliable and granular evaluation of healthcare centers. The evaluation is based on calculation of an expertise score for the healthcare centers. The expertise score is calculated based on expertise domain (ED) data derived from authentic, diverse and comprehensive databases. The raw data derived from such plurality of data sources is fed to a tree shaped paired neural network (TSPNN), along with a weight matrix which is derived using a machine learning model, for calculation of the expertise score. The expertise score derived in this manner is more accurate, useful, and interpretable, as compared to previously available evaluation benchmarks for healthcare centers. Also, the data derived from the plurality of databases is regularly updated by using API based updates, or online portal sync methodologies, thus providing up-to-date and quality data for expertise score calculation at all times.

Embodiments of the present disclosure may provide a system, a method and a computer program product for determining an expertise score for a healthcare center. The determination of the expertise score as disclosed in various embodiments described herein provides a reliable, accurate, granular and efficient strategy for evaluating a healthcare center, such as a hospital. This provides an end user, such as a patient or any user seeking medical care to make effective decisions related to their health and treatment needs, as they arise. These and other technical improvements of the invention will become evident from the description provided herein.

Some embodiments provide machine learning system evaluation of a healthcare center at various expertise levels, such as disease-specific medical expertise level or specialty-specific expertise level. The methods and systems disclosed herein enable differentiation of expertise levels among designated hospitals based on accurate and reliable medical data and comprehensive collection of data with adequate representation of domains related to medical expertise generation.

In some embodiments, a Tree Shape Paired Neural Network (TSPNN) model is disclosed.

An artificial neural network learning algorithm, or neural network, is generally a computational algorithm that is based on the concept of human biology of neurons and the way the neurons function to provide human brain with its intelligence capabilities. The neural network uses a network of functions to understand and translate a data input of one form into a desired output, in order to replicate the human neuron network. A weight is a parametric value or a coefficient in a matrix within a neural network that transforms input data within the network's hidden layers into an output value. A neural network comprises a series of nodes, or neurons, and each node further comprises a set of inputs, weight, and a bias value. As an input enters the node, it gets multiplied by a weight value and the resulting output is either observed, or passed to the next layer in the neural network The TSPNN is a neural network based on the concepts of using a machine learning model to extract weight for the TSPNN so that the TSPNN may be configured to enable extraction of various features of designated disease areas for the designated healthcare center. Further, in some embodiments, a differentiation network to determine disease-specific expertise level of a designated hospital is disclosed. The TSPNN and the differentiation network may enable evaluation of a healthcare center at disease-specific granularity.

The system, the method, and the computer program product facilitating evaluation and expertise score determination for a healthcare center are described with reference to FIG. 1 to FIG. 8.

FIG. 1 illustrates a schematic diagram of a network environment 100 of a system 101 for evaluating a healthcare center, in accordance with an example embodiment. The system 101 may be communicatively coupled to a plurality of data sources 103 via a network 105. The components described in the network environment 100 may be further broken down into more than one component such as one or more sensors or application in the system 101, which may be a user equipment and/or combined together in any suitable arrangement. Further, it is possible that one or more components may be rearranged, changed, added, and/or removed.

In an example embodiment, the system 101 may be embodied in one or more of several ways as per the required implementation. For example, the system 101 may be embodied as a cloud based service or a cloud based platform. In each of such embodiments, the system 101 may be communicatively coupled to the components shown in FIG. 1 to carry out the desired operations and wherever required modifications may be possible within the scope of the present disclosure. In various embodiments, the system 101 may be a backend server, a remotely located server, a cloud server, a data services platform, a platform providing a framework for data analysis, specifically medical data analysis or the like. To that end, the system 101 may be configured to provide a plurality of services related to data management and manipulation. Some of these services may include such as data collection, data cleansing, data organization, data labeling, data visualization, data analytics and data presentation (such as through dashboards). Further, the system 101 may also be configured to provide machine learning capabilities and Artificial Intelligence (AI) based products (such as AI bots) to the end users, which may be patients as well as healthcare centers or hospitals. The system 101 may be configured to provide all the above mentioned services based on data derived from a vast variety of sources and use the data to generate an expertise score for the healthcare center evaluations and insight provisioning.

The plurality of data sources 103 may comprise a data lake. The data lake may include scientifically sound, medically relevant and technically available data sources enabled by domain knowledge and industrial knowhow. These data sources may include, but are not limited to, databases and online portals such as Medical Subject Headings (MESH), Online Mendelian Inheritance in Man (OMIM), National Organization for Rare Disorders (NORD), Disease Ontology, MedlinePlus, National Institutes of Health (NIH), ClinicalTrials.gov, and Center for Medicare and Mediaid Services (CMS). The data in the data lakes as derived from the plurality of data sources 103 may be raw and unstructured. This raw data needs to be cleaned up before further processing. To that end, the system 101 is configured to perform cleaning and data preparation operations on the raw data. The system 101 is also configured to organize the raw data extracted from the plurality of data sources into one or more expertise domains (EDs) to obtain organized data values. Medical expertise is the knowledge, experience and know-how for a specific disease or disease area, including, but not limited to, its scientific foundation, pathogenic mechanism, and/or diagnostic, interventional or treatment options. Medical expertise is gained through a combined process of clinical practice, scientific research and translational medicine. This process helps to uncover scientific basis behind, invent novel interventional therapeutics, and improve diagnosis accuracy and treatment outcome. Medical expertise may be judged by one or more expertise domains as defined previously. These EDs majorly include three different EDs: a Scientific research expertise domain (SR or ED1), a Translational Medicine expertise domain (TM or ED2), and a Clinical practice expertise domain (CP or ED3). Clinical practice yields specific problems, Scientific research pursues answers to biological basis, and Translational medicine produces diagnostic and therapeutic solutions to improve the clinical outcome.

In some embodiments, the raw data extracted from the plurality of data sources 103 includes data values that fall into one of these three EDs.

In some embodiments, the raw data extracted from the plurality of data sources 103 comprises extracting raw data values associated with a healthcare condition. The healthcare condition may include one or more diseases which are treated by the healthcare center. The healthcare condition may further include a specialty area associated with treatment of various diseases by the healthcare center. The specialty areas include one or more disease specialty area comprising one or more diseases. For example, a specialty area may comprise Cardiology and Heart Surgery, Diabetes and Endocrinology, Ear Nose and Throat, Gastroenterology and GI surgery, Gynecology, Nephrology, Neurology and Neurosurgery, Oncology, Ophthalmology, Orthopedic and orthopedic surgery, Psychiatry, Pulmonology and Lung Surgery, Rheumatology, Urology, and the like.

In some embodiments, the raw data is organized into one or more EDs to obtain organized data values. The organized data is then further subjected to normalization based on a set of features of the raw data, and then a first data matrix corresponding to the organized data values for each of the one or more EDs is obtained. The first data matrix thus contains parametric data values obtained after normalization. The parametric data values may be associated with a health condition, which may be a disease or a specialty, as discussed earlier.

In some embodiments, some part of the raw data is also used for training of a machine learning model, which facilitates provision of a weight matrix, giving a set of coefficients determining an extent of contribution of each of the one or more parametric data values associated with the health condition for an expertise score determination. The expertise score determination may be performed by the system 101 associated with the health condition for expertise score determination. The determination may be based on the obtained first data matrix for each of the one or more EDs and the weight matrix corresponding to each first data matrix for each of the one or more EDs. The expertise score may be determined by using a neural network, such as a Tree Shaped Neural Network, as disclosed in conjunction with FIG. 6 and FIG. 7 described later.

In some embodiments, the expertise score determination performed by the system 101 may be used for evaluation of the healthcare center. The evaluation may be performed to assist users, such as patients, to make informed choices related to their treatment and thus improve the accuracy of critical decision making for the users.

In some example embodiments, the system 101 may be any user accessible device such as a mobile phone, a smartphone, a portable computer, a desktop computer, a laptop, a workstation, a tablet, a remote server, a cloud computing system, a computing platform and the like. The system 101 may comprise a processor, a memory and a communication interface. The processor, the memory and the communication interface may be communicatively coupled to each other. In such example embodiments, the system 101 may comprise processing means such as a central processing unit (CPU), storage means such as on-board read only memory (ROM) and random access memory (RAM). Additional, different, or fewer components may be provided. For example, the system 101 may be configured to execute and run mobile applications such as a messaging application, a browser application, a navigation application, a dashboard application, and the like. In one embodiment, the plurality of data sources 103 may be directly coupled to the system 101 via the network 105.

The network 105 may be wired, wireless, or any combination of wired and wireless communication networks, such as cellular, Wi-Fi, internet, local area networks, or the like. In one embodiment, the network 105 may include one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks (for e.g. LTE-Advanced Pro), 6G New Radio networks, ITU-IMT 2020 networks, code division multiple access (CDMA), wideband code division multiple access (WCDMA), wireless fidelity (Wi-Fi), wireless LAN (WLAN), Bluetooth, Internet Protocol (IP) data casting, satellite, mobile ad-hoc network (MANET), and the like, or any combination thereof.

In some embodiments, the system 101 may be coupled other computing systems and servers via the network 105 to provide expertise score determination and evaluation of the healthcare center.

FIG. 2 illustrates a block diagram of an architecture 200 of the system 101 of FIG. 1 for evaluating a healthcare center. As illustrated in the architecture 200, the system 101 may coupled to the plurality of data sources 103 for extracting raw data associated with one or more EDs, as discussed earlier. Further, the system 101 may be configured to perform one or more processing operations on the extracted raw data, for example using one or more modules of the system 101. These modules may exemplarily include such as a data platform module 101a, a data modeling module 101b, and a data analytics module 101c.

The data platform module 101a may be configured to perform one or more of data collection operations, data cleansing operations, and data organization operations. For example, the data platform module 101a may interface with the plurality of data sources 103, such as a data lake, through performing of queries for extracting raw data values. Once extracted, the data platform module 101a performs data cleansing to remove any inaccuracies, errors, incorrect data, incomplete data and duplicate data from the extracted data values. Further, the data platform module 101a may be configured to perform organization of the extracted raw but cleansed data into one or more EDs discussed earlier. Further, the one or more EDs may be associated with one or more health condition domains, such as common medical specialties, which were also discussed earlier. Additionally, the data platform module 101a may also have data values which are normalized to remove any outliers, based on a set of features of the raw data, and then arranged in the form of a first data matrix for each ED. Some of these features may include but are not limited to, Frontier research, Associated experts, Clinical excellence, Therapeutic investigation, and Federal support. The normalization is done based on maximum and minimum feature values. The data matrix for each ED, then contains normalized or parametric data values associated with the health condition.

The system 101 also includes the data modeling module 101b, which is configured to perform one or more operations related to data preparation for use in machine learning (ML). These operations may include such as data labeling, ML pair generation, model training, transfer learning and the like. In some embodiments, the data modeling module 101 may be configured to provide a weight matrix including a weigh coefficient for each data parametric data value included in the corresponding first data matrix. Further, the combination of the first data matrix and the weight matrix for each ED may be used to obtain an expertise score for the healthcare center, which may be used as an output data in further applications.

The system 101 also includes a data analytics module 101c which is configured to provide capabilities for integrative analysis and visualization of the output data. The analysis and visualization may be used in different scenarios 201, such as scenario A, scenario B, or scenario C, to provide various applications related to the output data. These applications may include such as healthcare center profile generation, healthcare center landscape generation, healthcare center comparison, disease area and specialty area analysis for the healthcare center and the like.

The system 101 also includes a product development module 203, which may utilize the services provided by the data analytics module 101c for offering various types of product development features and products for the healthcare center and user. These may include such as dashboards, interactive user interfaces (UIs), web portals, report publications (such as hospital ranking reports), recommendation or notification services for users (such as for treatment of a healthcare condition, based on the expertise score of the healthcare center), comparison of healthcare centers by disease area or specialty area and displaying the result of comparison on a user interface, and the like.

It may be understood that each of the modules 101a-101c of the system 101 may be implemented by a combination of various means, such as hardware, firmware, processor, circuitry, and/or other communication devices associated with execution of software including one or more computer program instructions. For example, one or more of the modules described above may be embodied by computer program instructions. In this regard, the computer program instructions which embody the procedures described above may be stored by a memory of the system 101, employing an embodiment of the present invention and executed by a processor.

FIG. 3 illustrates a block diagram of the system 101 for evaluating a healthcare center, in accordance with an example embodiment. The system 101 may include a storage means such as at least one memory 301 (hereinafter, also referred to as "memory 301"), a processing means such as at least one processor 303 (hereinafter, also referred to as "processor 303"), and a communication means such as at least one communication interface 305 (hereinafter, also referred to as "communication interface 305"). The processor 303 may retrieve computer program code instructions that may be stored in the memory 301 for execution of the computer program code instructions.

The processor 303 may be embodied in a number of different ways. For example, the processor 303 may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor 303 may include one or more processing cores configured to perform independently. A multi-core processor may enable multiprocessing within a single physical package. Additionally, or alternatively, the processor 303 may include one or more processors configured in tandem via the bus to enable independent execution of instructions, pipelining and/or multithreading.

In some embodiments, the processor 303 may be configured to provide Internet-of-Things (IoT) related capabilities to users of the system 101. Additionally, or alternatively, the processor 303 may include one or more processors capable of processing large volumes of workloads and operations to provide support for big data analysis. In an example embodiment, the processor 303 may be in communication with the memory 301 via a bus for passing information among components coupled to the system 101.

The memory 301 may be non-transitory and may include, for example, one or more volatile and/or non-volatile memories. In other words, for example, the memory 301 may be an electronic storage device (for example, a computer readable storage medium) comprising gates configured to store data (for example, bits) that may be retrievable by a machine (for example, a computing device like the processor 303). The memory 301 may be configured to store information, data, content, applications, instructions, or the like, for enabling the apparatus to carry out various functions in accordance with an example embodiment of the present invention. For example, the memory 301 may be configured to buffer input data related to ED matrix for processing by the processor 303. As exemplarily illustrated in FIG. 3, the memory 301 may be configured to store instructions for execution by the processor 303. As such, whether configured by hardware or software methods, or by a combination thereof, the processor 303 may represent an entity (for example, physically embodied in circuitry) capable of performing operations according to an embodiment of the present invention while configured accordingly. Thus, for example, when the processor 303 is embodied as an ASIC, FPGA or the like, the processor 303 may be specifically configured hardware for conducting the operations described herein. Alternatively, as another example, when the processor 303 is embodied as an executor of software instructions, the instructions may specifically configure the processor 303 to perform the algorithms and/or operations described herein when the instructions are executed. However, in some cases, the processor 303 may be a processor specific device (for example, a mobile terminal or a fixed computing device) configured to employ an embodiment of the present invention by further configuration of the processor 303 by instructions for performing the algorithms and/or operations described herein. The processor 303 may include, among other things, a clock, an arithmetic logic unit (ALU) and logic gates configured to support operation of the processor 303. The processor 303 may include one or more modules, such as a data preparation module 303A, a machine learning module 303B, a weight matrix module 303C, and a scoring and prediction module 303D.

The data preparation module 303A may be configured to provide capabilities and instructions related to data preparation and cleansing operations for raw data extracted from the plurality of data sources 103, as discussed earlier.

The machine learning module 303B may be configured to provide capabilities and instructions related to implementation and storage of a machine learning model for calculation of a weight matrix, as discussed earlier. The machine learning model may be any of the machine learning models implementing any of the machine learning algorithms known in the art such as a linear regression algorithm, a logistic regression algorithm, a decision tree, a random forest algorithm and the like.

The weight matrix module 303C may be configured to obtain and store the weight matrix provided by the machine learning module 303B, wherein the weight matrix comprises a set of coefficients determining an extent of contribution of each of the one or more parametric data values associated with the health condition for expertise score determination.

The scoring and prediction module 303D may be configured to use the input first data matrix corresponding to each ED and the corresponding weight matrix provided by the weight matrix module 303D and feed them to a tree-shaped paired neural network (TSPNN), which is discussed in conjunction with FIG. 6 and FIG. 7, for calculating an expertise score for the healthcare center, based on the input first data matrix and the weight matrix. The expertise score may then be output by the system 101 and accessed for various applications.

The system 101 may be accessed using the communication interface 305. The communication interface 305 may provide an interface for accessing various features and data stored in the system 101. The communication interface 305 may comprise input interface and output interface for supporting communications to and from the system 101. The communication interface 305 may be any means such as a device or circuitry embodied in either hardware or a combination of hardware and software that is configured to receive and/or transmit data to/from the system 101. In this regard, the communication interface 305 may include, for example, an antenna (or multiple antennae) and supporting hardware and/or software for enabling communications with a wireless communication network. Additionally, or alternatively, the communication interface 305 may include the circuitry for interacting with the antenna(s) to cause transmission of signals via the antenna(s) or to handle receipt of signals received via the antenna(s). In some environments, the communication interface 305 may alternatively or additionally support wired communication. As such, for example, the communication interface 305 may include a communication modem and/or other hardware and/or software for supporting communication via cable, digital subscriber line (DSL), universal serial bus (USB) or other mechanisms.

The communication interface 305 may also be used to provide access to various products provided by the product development module 203 of FIG. 2 and implementing the series of operations performed for calculating expertise score for a healthcare center, by the system 101.

FIG. 4 illustrates a block diagram of a series of operations performed by the system 101 of FIG. 1 for calculating an expertise score for a healthcare, in accordance with one or more example embodiments. Some of these operations have already been described in the embodiments disclosed above. More specific embodiments may be related to the series of operations as described in the following description.

Broadly, the system 101 may perform three major operations, data preparation 401, machine learning 403, and prediction 405.

Data preparation 401 may further include data labeling 401A and ML pair generation 401B for preparing training data for a machine learning model 403B and using the training data for training and learning of the machine learning model 403B. In some embodiments, the learning may be supervised learning, wherein the data labeling 401A and ML pair generation 401B is done under the supervision of a human expert. In some embodiments, the learning may be unsupervised learning, wherein the data labeling 401A and ML pair generation 401B is done without the intervention of the human expert, such as using various classification and clustering algorithms known in the art. Apart from preparing data for training of the machine learning model 403B, data preparation 401 also includes extracting disease area (DA) data 401C. DA data may refer to data associated with a specific disease area. The training data and the DA data are derived from raw data obtained from the plurality of databases 103 for a particular healthcare center, as discussed earlier. In some embodiments, the raw data is disease specific data 401D, which is organized into one of the three EDs: a scientific research expertise domain (SR or ED1), a translational medicine expertise domain (TM or ED2), and a clinical practice expertise domain (CP or ED3).

The machine learning operation 403 includes using the machine learning model 403B to obtain one or more weight matrices, such as one weight matrix 403A for each ED (ED1, ED2 and ED3). Further, the weight matrix 403A and the disease specific data 401D to an expertise score calculation module 405A for healthcare center's evaluation and also to perform the prediction operation 405 for various applications related to service delivery of the healthcare center.

In some embodiments, the expertise score calculation module 405A comprises the TSPNN, which uses a data matrix, ED, corresponding to each expertise domain and a corresponding weight matrix W, and to calculate the expertise score of a healthcare center or a hospital regarding a specific disease or a health condition.

Furthermore, this medical expertise equation can be used to calculate the expertise score for a disease area or a specialty (Y), which is a branch of medicine or surgery with similar characteristics biologically, or clinically, for a specific hospital.

FIG. 5 illustrates an exemplary table Table 1, showing various variables used in expertise score calculation equations Eq. 1 and Eq. 2 described above for a healthcare center, in accordance with one or more example embodiments.

The expertise score calculation as given in Eq. 1 may be done by the TSPNN illustrated in FIG. 6.

FIG. 6 illustrates an exemplary block diagram of a differential tree structure neural network model, such as a TSPNN 600 used for expertise score calculation for a healthcare center $H_i$.

The TSPNN 600 illustrates input data matrices state 601, such as ED from Table 1, used in combination with weight matrices state 603, such as W from Table 1, used for output state of expertise score calculation state 605, such as per Eq. 1 and/or Eq. 2, for the TSPNN 600.

In some embodiments, disease level data may be obtained based on the plurality of data sources 103, and organized to provide the input data matrices 601 comprising a first data matrix for each of the one or more EDs, wherein the corresponding first data matrix for each of the one or more EDs comprises one or more parametric data values associated with a health condition, such as for the disease.

In some embodiments, the weight matrices state 603 data comprises the weight matrix W, corresponding to each first data matrix for each of the one or more EDs, wherein the weight matrix comprises a set of coefficients determining an extent of contribution of each of the one or more parametric data values associated with the health condition for expertise score determination.

In some embodiments, at the expertise score calculation state 605, a plurality of product values based on the first data matrix, at input state 601, for each of the one or more EDs and the weight matrix, at weight matrices state 603, for each first data matrix of the one or more EDs, are multiplied to provide one product value for each ED based on the product of the corresponding first data matrix and the weight matrix. Further, these product values are integrated, such as using the Eq. 1 or Eq. 2, to obtain the expertise score for the healthcare center.

The expertise score calculation may also be utilized for comparing two hospitals, as illustrated in FIG. 7.

FIG. 7 illustrates an exemplary block diagram of a differential tree structure paired neural network model, TSPNN model 700, used for obtaining weight matrix for expertise score comparison between two healthcare centers $H_m$ and $H_n$. As illustrated in the TSPNN model 700, at input stage 701, data matrices for two healthcare centers Hm and Hn are given as input for each of the one or more EDs (ED1, ED2 and ED3), and multiplied with their corresponding weights at a weight matrix state 703. In some embodiments, $H_m$ is considered as a first healthcare center and $H_n$ is considered a second healthcare center such that a set of historical coefficient values for the weight matrix corresponding to $H_m$ and $H_n$ are already known. The historical coefficient values are determined and/or are known based on a historical first expertise score associated with the first healthcare center, $H_m$ and a historical second expertise score associated with the second healthcare center, $H_n$. For example, based on previous records or historical data from past calculations, it may be known that there are two different groups of hospitals, like "top hospitals" and "average hospitals". Further, the rating of individual hospitals in each group may be previously known, and in fact, may be used as the basis for segregating the hospitals into different groups. The "top hospitals" may be, such as, a group of top 3% hospitals. Accordingly, the set of historical coefficient values based on previously known weights w1-w9 for $H_m$ (which may be one of the "top hospitals") may be used to determine the set of coefficients α, β, and γ, which are the current set of coefficients of the weight matrix. α, β, and γ determine the extent of contribution of each of the one or more parametric data values of each normalized data matrix ED (associated with the health condition) for expertise score determination.

Further, Hn may belong to the group of "average hospitals" and accordingly, since it is known that Hm is a better rated hospital than Hn, so the historical first expertise score associated with the first healthcare center or hospital, Hm may be greater than the historical second expertise score associated with the second healthcare center or hospital Hn. Based on this knowledge, and using a machine learning model (such as the machine learning module 303B), a current first expertise score for the first healthcare center or hospital, Hm and a current second expertise score for the second healthcare center or hospital Hn based on the obtained first data matrix for each of the one or more EDs (having values x1-x9) and the weight matrix corresponding to each first data matrix for each of the one or more EDs (having values w1-w9), and the set of historical coefficient values. α, β, and γ may be calculated.

In some embodiments, the current expertise scores of the first healthcare center, Hm, and the second healthcare center, Hn, may be obtained using the expertise calculation equation as follows (Eq. 3):

$$\text{score} = \begin{bmatrix} \alpha & \beta & \gamma \end{bmatrix} \begin{bmatrix} \tanh((x_1, x_2, x_3) - (w_1, w_2, w_3)' + b_1) \\ \tanh((x_4, x_5, x_6) - (w_4, w_5, w_6)' + b_2) \\ \tanh((x_7, x_8, x_9) - (w_7, w_8, w_9)' + b_3) \end{bmatrix} \quad \text{(Eq. 3)}$$

Based on the obtained scores, the current first expertise score of Hm may be compared with the historical first expertise score of Hm. Similarly the current second expertise score of Hn may be compared with the historical second expertise score of Hn. This may be done to check the validity of the determined weight matrix coefficients α, β, and γ.

In some embodiments, the current first expertise score of Hm and the current second expertise score of Hn may be determined at stage 705 of the TSPNN model 700. These scores may be further sent to output stage 707, as output 1 and output 2. If Hm, which was the better hospital in this case, is obtained as the output at output 1, then it is determined that the weights α, β, and γ were appropriate. Then, another pair of hospitals is selected the whole process is repeated.

However, if Hm is not obtained at output-1, then it is an indication that weight values α, β, and γ need to be adjusted f and re-run the TSPNN until the better hospital is output to "output-1." By repeating the algorithm for all combinations of the "top hospitals" and "ordinary hospitals" to check if the outputs are correct, the correct weight coefficients can be determined.

One of the ways to check the validity of weights may be to provide the weight matrix comprising the set of historical coefficient values, based on a result of the comparison of: the current first expertise score of Hm with the historical first expertise score of Hm; and the current second expertise score of Hn with the historical second expertise score of Hn.

In some embodiments, this comparison may further comprise: determining a first difference value between the first expertise score and the historical first expertise score; and determining a second difference value between the second expertise score and the historical second expertise score. These difference values may be then compared with a first difference value threshold and a second difference value threshold respectively. Further, if these differences are more than the respective threshold values (even in one these comparisons), then it means the historical weights need to be adjusted.

Thus, using the comparison of the expertise scores of the first healthcare center and the second healthcare center with their respective historical expertise scores, the weight matrix corresponding to each of the one or more EDs, for the health condition level (that is disease level or specialty level), may be determined. The determined weight matrix is then used by the TSPNN model 600 as shown in FIG. 6, for expertise score calculation of the healthcare center Hi.

FIG. 8 illustrates an exemplary flow diagram of a method 800 for expertise score determination of a healthcare center, in accordance with an example embodiment. It will be understood that each block of the flow diagram of method 800 may be implemented by various means, such as hardware, firmware, processor, circuitry, and/or other communication devices associated with execution of software including one or more computer program instructions. For example, one or more of the procedures described above may be embodied by computer program instructions. In this regard, the computer program instructions which embody the procedures described above may be stored by a memory 301 of the system 101, employing an embodiment of the present invention and executed by the processor 305. As will be appreciated, any such computer program instructions may be loaded onto a computer or other programmable apparatus (for example, hardware) to produce a machine, such that the resulting computer or other programmable apparatus implements the functions specified in the flow diagram blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flow diagram blocks.

Accordingly, blocks of the flow diagram support combinations of means for performing the specified functions and combinations of operations for performing the specified functions for performing the specified functions. It will also be understood that one or more blocks of the flow diagram, and combinations of blocks in the flow diagram, may be implemented by special purpose hardware-based computer systems which perform the specified functions, or combinations of special purpose hardware and computer instructions. The method 800 illustrated by the flowchart diagram of FIG. 8 is for determining an expertise score for a healthcare center. Fewer, more, or different steps may be provided.

In accordance with method 800, at step 801, raw data values are extracted. The raw data values may include raw data related to a plurality of features about various diseases and specialty areas for the healthcare center. The raw data may be obtained from a plurality of data sources, such as the plurality of data sources 103, including but not limited to databases and online portals such as Medical Subject Headings (MESH), Online Mendelian Inheritance in Man (OMIM), National Organization for Rare Disorders (NORD), Disease Ontology, MedlinePlus, National Institutes of Health (NIH), ClinicalTrials.gov, Center for Medicare and Mediaid Services (CMS), National Cancer Institute (NCI), Food and Drug Administration (FDA), Centers for Disease Control and Prevention (CDC).

Further, at step 803, the raw data may be organized into one or more expertise domains to obtain organized data values. The one or more expertise domains may include such as a scientific research expertise domain (SR or ED1), a translational medicine expertise domain (TM or ED2), a clinical practice expertise domain (CP or ED3), or a combination thereof. In some further examples, the expertise domains are expandable to other data source, such as real-world evidence data, pharmacovigilance, IoT data, health data from wearable devices. The adoption of expandable data is for adequate representation.

Then, at step 805, the organized data values may be normalized to obtain a first data matrix for each of the one or more EDs. Thus, after step 805, three first data matrices ED1, ED2, and ED3 may be obtained, one for each expertise domain. Each of the three first data matrices comprise one or more parametric data values associated with a health condition (such as a disease X or a specialty Y mentioned in table 1 of FIG. 5) for the healthcare center, wherein the parametric data values are normalized values obtained after removing outliers.

Further, at step 807, a weight matrix may be obtained using a machine learning model. At this step, one weight matrix corresponding to each first data matrix for each of the one or more EDs is derived using machine learning, such as using the machine learning model 403B disclosed in FIG. 4. The weight matrix comprises a set of coefficients determining an extent of contribution of each of the one or more parametric data values associated with the health condition for expertise score determination. Weights may be given as numerical values ranging between 0 and 1.

Finally, at step 809, the expertise score for the healthcare center is calculated based on the weight matrix obtained at step 807, and the first data matrix obtained at step 805, for each expertise domain. The first data matrix and the weight matrix may be fed to the TSPNN model 600 disclosed in FIG. 6, and the final expertise score may be calculated using any of the equations Eq. 1 or Eq. 2, for the specific granularity level required for the health condition and the healthcare center.

Thus, using the methods and system disclosed in the embodiments described above, a reliable, granular, trust worthy, efficient and up-to-date evaluation mechanism may be provided for healthcare centers, such as for public hospital evaluation. The expertise score for any healthcare center determined using the various embodiments disclosed herein also provide enhance care quality, and possibly improve the outcome of healthcare processes and treatment related admissions to healthcare centers. This further helps to improve overall performance of the healthcare system and critical decision making processes during illness by improving both the pathways of healthcare access: selection pathway and care pathway. Using the expertise score comparison embodiment discussed in FIG. 7, the patient will be able to choose a high-quality hospital with higher expertise score and thus improving the selection pathway. Further, only provision of good care will lead to better reputation and review data for the hospital, which is further updated on a frequent basis and used for expertise score calculation, thereby only good care will lead to higher scoring data.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

I claim:

1. A computer-implemented method for determining an expertise score for a healthcare center, comprising:
   extracting raw data values from a plurality of data sources;
   organizing, using a processor, the extracted raw data values into one or more expertise domains (EDs) to obtain organized data values, wherein the one or more EDs comprise at least a scientific research expertise domain (SR or ED1), a translational medicine expertise domain (TM or ED2), a clinical practice expertise domain (CP or ED3), or a combination thereof;
   normalizing the organized data values based on a set of features to obtain a first data matrix for each of the one or more EDs, wherein the corresponding first data matrix for each of the one or more EDs comprises one or more parametric data values associated with a health condition;
   generating machine learning (ML) pair data from the extracted raw data, wherein the ML pair data includes data matrices for a pair of healthcare centers, and wherein the healthcare center is included in the pair of healthcare centers;
   training a tree shaped paired machine learning (TSPNN) model based on the generated ML pair data;
   obtaining, using the trained TSPNN model executed by the processor, a weight matrix corresponding to each first data matrix for each of the one or more EDs, wherein the weight matrix comprises a set of coefficients determining an extent of contribution of each of the one or more parametric data values associated with the health condition for expertise score determination, wherein the set of coefficients is determined based on a set of historical coefficient values,
   the set of historical coefficients is based on a historical expertise score associated with the healthcare center; and
   calculating, using the processor, the expertise score for the healthcare center based on the obtained first data matrix for each of the one or more Eds and the weight matrix corresponding to each first data matrix for each of the one or more Eds.

2. The computer-implemented method of claim 1, wherein calculating the expertise score for the first healthcare center further comprises:
   determining, using the processor, a plurality of product values based on the first data matrix for each of the one or more Eds and the weight matrix for each first data matrix of the one or more Eds, wherein the plurality of product values comprise one product value for each ED based on the product of the corresponding first data matrix and the weight matrix; and
   integrating, using the processor, the plurality of product values to obtain the expertise score for the healthcare center.

3. The computer-implemented method of claim 1, wherein extracting raw data values from a plurality of data sources comprises extracting raw data values associated with a healthcare condition from the plurality of data sources.

4. The computer-implemented method of claim 3, wherein the healthcare condition comprises one or more diseases, and the expertise score for the healthcare center comprises the expertise score for the one or more diseases.

5. The computer-implemented method of claim 4, wherein the healthcare condition is a disease specialty comprising one or more diseases, and the expertise score for the healthcare center comprises the expertise score for the disease specialty.

6. The computer-implemented method of claim 1, wherein obtaining the weight matrix corresponding to each first data matrix for each of the one or more Eds comprises:
obtaining, for each of a first healthcare center and a second healthcare center, a set of historical coefficient values of the weight matrix,
wherein the set of historical coefficient values are derived based on a historical first expertise score associated with the first healthcare center and a historical second expertise score associated with the second healthcare center,
and wherein the historical first expertise score is greater than the historical second expertise score;
calculating, using the TSPNN model executed by the processor, a current first expertise score for the first healthcare center and a current second expertise score for the second healthcare center based on the obtained first data matrix for each of the one or more Eds and the weight matrix corresponding to each first data matrix for each of the one or more Eds, wherein the weight matrix comprises the set of historical coefficient values;
comparing, using the TSPNN model executed by the processor, the current first expertise score with the historical first expertise score, and the current second expertise score with the historical second expertise score; and
providing, based on a result of the comparison, the weight matrix comprising the set of historical coefficient values, wherein the set of historical coefficient values are used as the set of coefficients determining the extent of contribution of each of the one or more parametric data values associated with the health condition for expertise score determination.

7. The computer-implemented method of claim 6, further comprising:
determining a first difference value between the first expertise score and the historical first expertise score;
determining a second difference value between the second expertise score and the historical second expertise score;
obtaining a first difference value threshold and a second difference value threshold;
adjusting the set of historical weight coefficient values when at least one of the first difference value or the second difference value is more than the first difference value threshold and the second difference value threshold, respectively.

8. The computer-implemented method of claim 1, further comprising:
providing a recommendation to a user for treatment of a healthcare condition, based on the expertise score of the healthcare center.

9. The computer-implemented method of claim 1, wherein the TSPNN model comprises a neural network model.

10. A system for determining an expertise score for a healthcare center, the system comprising:
a memory configured to store computer executable instructions; and
one or more processors configured to execute the computer executable instructions to:
extract raw data values from a plurality of data sources;
organize the extracted raw data values into one or more expertise domains (Eds) to obtain organized data values, wherein the one or more Eds comprise at least a scientific research expertise domain (SR or ED1), a translational medicine expertise domain (TM or ED2), a clinical practice expertise domain (CP or ED3), or a combination thereof;
normalize the organized data values based on a set of features to obtain a first data matrix for each of the one or more Eds, wherein the corresponding first data matrix for each of the one or more Eds comprises one or more parametric data values associated with a health condition;
generate machine learning (ML) pair data from the extracted raw data, wherein the ML pair data includes data matrices for a pair of healthcare centers, and wherein the healthcare center is included in the pair of healthcare centers;
train a tree shaped paired machine learning (TSPNN) model based on the generated ML pair data;
obtain, using the trained TSPNN, a weight matrix corresponding to each first data matrix for each of the one or more Eds, wherein the weight matrix comprises a set of coefficients determining an extent of each of the one or more parametric data values associated with the health condition for expertise score determination, wherein the set of coefficients is determined based on a set of historical coefficient values,
the set of historical coefficients is based on a historical expertise score associated with the healthcare center; and
calculate the expertise score for the healthcare center based on the obtained first data matrix for each of the one or more Eds and the weight matrix corresponding to each first data matrix for each of the one or more Eds.

11. The system of claim 10, wherein to calculate the expertise score for the healthcare center, one or more processors configured to execute the computer executable instructions to:
determine, a plurality of product values based on the first data matrix for each of the one or more Eds and the weight matrix for each first data matrix of the one or more Eds, wherein the plurality of product values comprise one product value for each ED based on the product of the corresponding first data matrix and the weight matrix; and
integrate the plurality of product values to obtain the expertise score for the healthcare center.

12. The system of claim 10, wherein extracting raw data values from a plurality of data sources comprises extracting raw data values associated with a healthcare condition from the plurality of data sources.

13. The system of claim 12, wherein the healthcare condition comprises one or more diseases, and the expertise score for the healthcare center comprises the expertise score for the one or more diseases.

14. The system of claim 13, wherein the healthcare condition is a disease specialty comprising the one or more diseases, and the expertise score for the healthcare center comprises the expertise score for the disease specialty.

15. The system of claim 10, wherein to obtain the weight matrix, the one or more processors are further configured to execute the instructions to:
- obtain, for each of a first healthcare center and a second healthcare center, a set of historical coefficient values of the weight matrix,
- wherein the set of historical coefficient values are derived based on a historical first expertise score associated with the first healthcare center and a historical second expertise score associated with the second healthcare center,
- and wherein the historical first expertise score is greater than the historical second expertise score;
- calculate, using the TSPNN model executed by the one or more processors, a current first expertise score for the first healthcare center and a current second expertise score for the second healthcare center based on the obtained first data matrix for each of the one or more Eds and the weight matrix corresponding to each first data matrix for each of the one or more Eds, wherein the weight matrix comprises the set of historical coefficient values;
- compare, using the TSPNN model executed by one or more processors, the current first expertise score with the historical first expertise score, and the current second expertise score with the historical second expertise score; and
- provide, based on a result of the comparison, the weight matrix comprising the set of historical coefficient values, wherein the set of historical coefficient values are used as the set of coefficients determining the extent of contribution of each of the one or more parametric data values associated with the health condition for expertise score determination.

16. The system of claim 15, wherein the one or more processors are further configured to execute the instructions to:
- determine a first difference value between the first expertise score and the historical first expertise score;
- determine a second difference value between the second expertise score and the historical second expertise score;
- obtain a first difference value threshold and a second difference value threshold;
- adjust the set of historical weight coefficient values when at least one of the first difference value or the second difference value is more than the first difference value threshold and the second difference value threshold, respectively.

17. The system of claim 10, wherein the one or more processors configured to execute the computer executable instructions to: provide a recommendation to a user for treatment of a healthcare condition, based on the expertise score of the healthcare center.

18. The system of claim 10, wherein the TSPNN model comprises a neural network model.

19. A computer programmable product comprising a non-transitory computer readable medium having stored thereon computer executable instructions which when executed by one or more processors, cause the one or more processors to carry out operations for determining an expertise score for a healthcare center, the operations comprising:
- extracting raw data values from a plurality of data sources;
- organizing, the extracted raw data values into one or more expertise domains (Eds) to obtain organized data values, wherein the one or more Eds comprise at least a scientific research expertise domain (SR or ED1), a translational medicine expertise domain (TM or ED2), a clinical practice expertise domain (CP or ED3), or a combination thereof;
- normalizing the organized data values based on a set of features to obtain a first data matrix for each of the one or more Eds, wherein the corresponding first data matrix for each of the one or more Eds comprises one or more parametric data values associated with a health condition;
- generating machine learning (ML) pair data from the extracted raw data, wherein the ML pair data includes data matrices for a pair of healthcare centers, and wherein the healthcare center is included in the pair of healthcare centers;
- training a tree shaped paired machine learning (TSPNN) model based on the generated ML pair data;
- obtaining, using the trained TSPNN model, a weight matrix corresponding to each first data matrix for each of the one or more Eds, wherein the weight matrix comprises a set of coefficients determining an extent of each of the one or more parametric data values associated with the health condition for expertise score determination, wherein the set of coefficients is determined based on a set of historical coefficient values,
- the set of historical coefficients is based on a historical expertise score associated with the healthcare center; and
- calculating, the expertise score for the healthcare center based on the obtained first data matrix for each of the one or more EDs and the weight matrix corresponding to each first data matrix for each of the one or more EDs.

20. The computer programmable product of claim 19, wherein the operations further comprising:
- determining, a plurality of product values based on the first data matrix for each of the one or more EDs and the weight matrix for each first data matrix of the one or more EDs, wherein the plurality of product values comprise one product value for each ED based on the product of the corresponding first data matrix and the weight matrix; and
- integrating, the plurality of product values to obtain the expertise score for the healthcare center.

* * * * *